(12) United States Patent
Yano

(10) Patent No.: US 10,238,632 B2
(45) Date of Patent: Mar. 26, 2019

(54) SIGMA RECEPTOR-BINDING AGENT

(71) Applicant: FUJIFILM Toyama Chemical Co., Ltd., Tokyo (JP)

(72) Inventor: Takeaki Yano, Toyama (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/735,022

(22) PCT Filed: Jun. 10, 2016

(86) PCT No.: PCT/JP2016/067308
§ 371 (c)(1),
(2) Date: Dec. 8, 2017

(87) PCT Pub. No.: WO2016/199878
PCT Pub. Date: Dec. 15, 2016

(65) Prior Publication Data
US 2018/0153855 A1   Jun. 7, 2018

(30) Foreign Application Priority Data

Jun. 11, 2015 (JP) .................................. 2015-118641

(51) Int. Cl.
*A61K 31/397* (2006.01)
(52) U.S. Cl.
CPC .................................. *A61K 31/397* (2013.01)
(58) Field of Classification Search
CPC ................................................ A61K 31/397
USPC ..................................................... 514/210.19
See application file for complete search history.

(56) References Cited

U.S. PATENT DOCUMENTS

| | | |
|---|---|---|
| 2003/0212094 A1 | 11/2003 | Yamabe et al. |
| 2005/0070521 A1 | 3/2005 | Saitoh et al. |
| 2006/0205709 A1 | 9/2006 | Kimura et al. |
| 2009/0093453 A1 | 4/2009 | Iwakami et al. |
| 2010/0184997 A1 | 7/2010 | Fukushima et al. |
| 2013/0158029 A1 | 6/2013 | Garcia López et al. |
| 2015/0031678 A1 | 1/2015 | Diaz Fernández et al. |

FOREIGN PATENT DOCUMENTS

| | | |
|---|---|---|
| EP | 1437353 A1 | 7/2004 |
| EP | 1614419 A1 | 1/2006 |
| EP | 2011796 A1 | 1/2009 |
| EP | 2048145 A1 | 4/2009 |
| JP | 2013-528171 A | 7/2013 |
| JP | 2015-508089 A | 3/2015 |
| WO | 01/64670 A1 | 9/2001 |
| WO | 03/035647 A1 | 5/2003 |
| WO | 2004/091605 A1 | 10/2004 |
| WO | 2007/125913 A1 | 11/2007 |
| WO | 2008/016107 A1 | 2/2008 |

OTHER PUBLICATIONS

Nguyen et al., "Role of sigma-1 receptors in neurodegenerative diseases", Journal of Pharmacological Sciences, 2015, vol. 127, pp. 17-29.
Huang et al., "Sigma-2 Receptor Ligands and Their Perspectives in Cancer Diagnosis and Therapy", Medicinal Research Reviews, 2014, vol. 34, No. 3, pp. 532-566.
Izzo et al., "Alzheimer's Therapeutics Targeting Amyloid Beta 1-42 Oligomers II: Sigma-2/PGRMC1 Receptors Mediate Abeta 42 Oligomer Binding and Synaptotoxicity", PLOS ONE, Nov. 2014, vol. 9, Issue 11, e111899, pp. 1-15.
Guitart et al., "Sigma receptors: biology and therapeutic potential", Psychopharmacology, 2004, vol. 174, pp. 301-319 (total 20 pages).
International Search Report dated Aug. 30, 2016, issued by the International Searching Authority in Application No. PCT/JP2016/067308.
International Preliminary Report on Patentability with translation of Written Opinion dated Dec. 12, 2017, issued by the International Searching Authority in Application No. PCT/JP2016/067308.
Extended European Search Report dated May 29, 2018, from the European Patent Office in counterpart European Application No. 16807583.6.
Takamura, Yusaku et al: "Effects of the neurotrophic agent T-817MA on oligomeric amyloid-[beta]-induced deficits in long-term potentiation in the hippocampal CA1 subfield.", Neurobiology of Aging, Mar. 2014, vol. 35, No. 3, pp. 532-536 (5 pages total).
Takashi Uehara et al:"T-817MA, but Not Haloperidol and Risperidone, Restores Parvalbumin-Positive [gamma]-Aminobutyric Acid Neurons in the Prefrontal Cortex and Hippocampus of Rats Transiently Exposed to MK-801 at the Neonatal Period", ISRN Psychiatry, 2012, pp. 1-8, vol. 2012 (8 pages total).
Yano, Takeaki et al: "Sigma-1 receptor is a molecular target for novel neuroprotectant T-817MA", Alzheimer's & Dementia: The Journal of the Alzheimer's Association, Jul. 2015, vol. 11, No. 7, p. P861.

Primary Examiner — Yevgeny Valenrod
(74) Attorney, Agent, or Firm — Sughrue Mion, PLLC

(57) ABSTRACT

A sigma receptor-binding agent, which comprises an alkyl ether derivative represented by formula [1] or a salt thereof is provided.

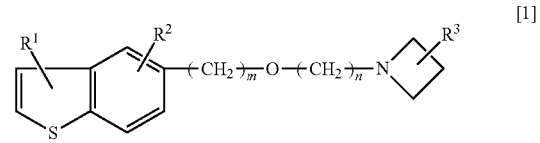

wherein $R^1$ and $R^2$, which are the same or different, each represent a hydrogen atom, a halogen atom, an optionally substituted $C_{1-6}$ alkyl group, an optionally substituted aryl group, or the like; $R^3$ represents an optionally protected hydroxyl group or the like; m and n, which are the same or different, each represent an integer of 1 to 6.

13 Claims, No Drawings

SIGMA RECEPTOR-BINDING AGENT

CROSS REFERENCE TO RELATED APPLICATIONS

This application is a National Stage of International Application No. PCT/JP2016/067308 filed Jun. 10, 2016, claiming priority based on Japanese Patent Application No. 2015-118641 filed Jun. 11, 2015, the contents of all of which are incorporated herein by reference in their entirety.

TECHNICAL FIELD

The present invention relates to an alkyl ether derivative or a salt thereof which is useful as a sigma receptor-binding agent. The present invention also relates to a method of activating or inhibiting a sigma receptor using an alkyl ether derivative or a salt thereof.

BACKGROUND ART

It is known that sigma receptors are expressed in central nervous cells, etc., and adjust a number of biological mechanisms involved in neurodegeneration (Non Patent Literature 1). Two subtypes of sigma receptors (sigma 1 and sigma 2) are known, and they can be distinguished by different pharmacological profiles and molecular characteristics.

Sigma-1 receptors are present in the nucleus of the central nervous system, several types of central nervous cells (astrocytes, microglia, and oligodendrocytes), and the central nervous system-related immune and endocrine tissues. The receptors are considered to be involved in a plurality of physiological and pathological pathways. However, the roles of sigma-1 receptors in the individual pathways have not yet been elucidated.

Sigma-2 receptors have been identified also in central nervous cells and are largely present, especially in proliferating cells or tissues of tumors, etc. The receptors are considered to regulate the growth of tumor cells (Non Patent Literature 2). Meanwhile, it has also been reported that sigma-2 receptors are involved in adhesion to amyloid beta cells (Non Patent Literature 3).

Known sigma-1 receptor antagonists are BD1047 (N-[2-(3,4-dichlorophenyl)ethyl]-N-methyl-2-(dimethylamino) ethylamine), BD1063 (1-[2-(3,4-dichlorophenyl)ethyl]-4-methylpiperazine), and NE-100 (4-methoxy-3-(2-phenylethoxy)-N,N-dipropylbenzene ethaneamine). Meanwhile, known sigma-1 receptor agonists are (+)-pentazocine, (+)-SKF10,047 (N-allylnormetazocine), PRE084 (2-morpholin-4-ylethyl-1-phenylcyclohexane-1-carboxylate), and SA4503 (1-[2-(3,4-dimethoxyphenyl)ethyl]-4-(3-phenylpropyl)piperazine). Many commercially available drugs (e.g., haloperidol, donepezil, and fluvoxamine) interact with sigma-1 receptors. However, there are not many publicly known compounds which selectively have a high affinity for the sigma-1 receptor.

It is widely known that many of sigma-1 receptor ligands bind to sigma-2 receptors. The same applies to many of the compounds described above. Meanwhile, sigma-2-receptor-selective ligands, such as Siramesine (1'-{4-[1-(4-fluorophenyl)-1H-indol-3-yl]butyl}-3H-spiro[2-benzofuran-1,4'-piperidine]), and PB28(1-cyclohexyl-4-[3-(5-methoxy-1,2,3,4-tetrahydronaphthalen-1-yl)propyl]piperazine), have been developed.

To date, it has been known that alkyl ether derivatives described in Patent Literature 1 and 2 have the neuroprotective action, neuroregenerative action, neurite outgrowth-promoting action, and neurogenesis-inducing action.

PRIOR ART LITERATURES

Patent Literatures

Patent Literature 1: WO 03/035647
Patent Literature 2: WO 2007/125913

Non Patent Literatures

Non Patent Literature 1: Journal of Pharmacological Sciences, vol. 127, pp. 17-29 (2015)
Non Patent Literature 2: Medicinal Research Reviews, vol. 34, pp. 532-566 (2013)
Non Patent Literature 3: PLoS One, vol. 9, e111899 (2014)

DISCLOSURE OF INVENTION

Problem to be Solved by the Invention

A compound having a high affinity for a sigma receptor and a method of activating or inhibiting a sigma receptor using such compound have been awaited.

Solution to Problem

Under such circumstances, as a result of intensive studies, the present inventors found that a sigma receptor-binding agent which comprises an alkyl ether derivative represented by the following formula [1] or a salt thereof has a high affinity for sigma receptors and thus is useful as a sigma receptor-binding agent:

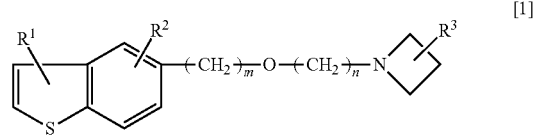

wherein $R^1$ and $R^2$, which are the same or different, each represent at least one member selected from the group consisting of a hydrogen atom, a halogen atom, an optionally substituted $C_{1-6}$ alkyl group, an optionally substituted aryl group, an optionally substituted ar($C_{1-6}$)alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group, and an oxo group; $R^3$ represents an optionally substituted $C_{1-6}$ alkylamino group, an optionally protected amino group, or an optionally protected hydroxyl group; m and n, which are the same or different, each represent an integer of 1 to 6. This has led to the completion of the present invention.

According to the present invention, the following invention is provided.

(1) A sigma receptor-binding agent, which comprises an alkyl ether derivative represented by the formula [1] or a salt thereof.
(2) A sigma-1 receptor-binding agent, which comprises an alkyl ether derivative represented by the formula [1] or a salt thereof.
(3) The sigma-1 receptor-binding agent according to (2), wherein $R^1$ and $R^2$, which are the same or different, each represent a hydrogen atom, a halogen atom, or a $C_{1-6}$ alkoxy group.
(4) The sigma-1 receptor-binding agent according to (2) or (3), wherein m is 2 and n is 2 or 3.
(5) The sigma-1 receptor-binding agent according to any one of (2) to (4), wherein $R^3$ is an optionally protected hydroxyl group.
(6) The sigma-1 receptor-binding agent according to (2), wherein the alkyl ether derivative is 1-(3-(2-(1-benzothiophene-5-yl)ethoxy)propyl)azetidine-3-ol.
(7) A sigma-2 receptor-binding agent, wherein the alkyl ether derivative comprises 1-(3-(2-(1-benzothiophene-5-yl)ethoxy)propyl)azetidine-3-ol or a salt thereof.
(8) A method of using an alkyl ether derivative represented by the formula [1] or a salt thereof for activation or inhibition of a sigma receptor.
(9) A method of using an alkyl ether derivative represented by the formula [1] or a salt thereof for activation or inhibition of a sigma-1 receptor.
(10) The method according to (9), wherein $R^1$ and $R^2$, which are the same or different, each represent a hydrogen atom, a halogen atom, or a $C_{1-6}$ alkoxy group.
(11) The method according to (9) or (10), wherein m is 2 and n is 2 or 3.
(12) The method according to any one of (9) to (11), wherein $R^3$ is an optionally protected hydroxyl group.
(13) The method according to (9), wherein the alkyl ether derivative is 1-(3-(2-(1-benzothiophene-5-yl)ethoxy)propyl)azetidine-3-ol.
(14) A method of using 1-(3-(2-(1-benzothiophene-5-yl)ethoxy)propyl)azetidine-3-ol or a salt thereof for activation or inhibition of a sigma-2 receptor.

The following invention is also provided according to the present invention.
(a) Use of an alkyl ether derivative represented by the formula [1] or a salt thereof for production of a sigma receptor-binding agent.
(b) A laboratory reagent, which comprises an alkyl ether derivative represented by the formula [1] or a salt thereof for investigating the physiological function and/or physiological activity of sigma receptors.
(c) A reference substance, which comprises an alkyl ether derivative represented by the formula [1] or a salt thereof for determining the sigma receptor activity of a sample.
(d) A method of using an alkyl ether derivative represented by the formula [1] or a salt thereof for investigating the physiological function and/or activity of sigma receptors.
(e) A method of using an alkyl ether derivative represented by the formula [1] or a salt thereof for determining the sigma receptor activity of a sample.

Advantageous Effects of Invention

An alkyl ether derivative represented by the formula [1] or a salt thereof according to the present invention has a high affinity to a sigma receptor, and it is useful as a sigma receptor-binding agent.

A method of using an alkyl ether derivative represented by the formula [1] or a salt thereof according to the present invention is useful as a method of activating or inhibiting a sigma receptor.

EMBODIMENTS FOR CARRYING OUT THE INVENTION

The present invention is explained in detail below.
The terms used herein have the following meanings, unless otherwise specified.
The term "halogen atom" refers to a fluorine atom, chlorine atom, bromine atom, or iodine atom.
The term "$C_{1-6}$ alkyl group" refers to linear or branched $C_{1-6}$ alkyl groups such as methyl, ethyl, propyl, isopropyl, butyl, isobutyl, tert-butyl, pentyl, and hexyl.
The term "$C_{2-6}$ alkenyl group" refers to $C_{2-6}$ alkenyl groups such as vinyl, propenyl, butenyl, pentenyl, and hexenyl.
The term "acyl $C_{1-6}$ alkyl group" refers to acyl $C_{1-6}$ alkyl groups such as acetylmethyl, benzoylmethyl, p-nitrobenzoylmethyl, p-bromobenzoylmethyl, p-methoxybenzoylmethyl, and 1-benzoylethyl.
The term "acyloxy $C_{1-6}$ alkyl group" refers to acyloxy $C_{1-6}$ alkyl groups such as acetoxymethyl, propionyloxymethyl, and pivaloyloxymethyl.
The term "arylthio $C_{1-6}$ alkyl" group refers to groups such as phenylsulfenylmethyl and 2-(p-nitrophenylsulfenyl)ethyl.
The term "arylsulfonyl $C_{1-6}$ alkyl group" refers to arylsulfonyl $C_{1-6}$ alkyl groups such as p-toluenesulfonylethyl.
The term "nitrogen-containing heterocyclic $C_{1-6}$ alkyl group" refers to nitrogen-containing heterocyclic $C_{1-6}$ alkyl groups such as phthalimidomethyl and succinimidemethyl.
The term "$C_{3-8}$ cycloalkyl group" refers to $C_{3-8}$ cycloalkyl groups such as cyclopropyl, cyclobutyl, cyclopentyl, and cyclohexyl.
The term "$C_{1-6}$ alkylthio $C_{1-6}$ alkyl group" refers to $C_{1-6}$ alkylthio $C_{1-6}$ alkyl groups such as methylthiomethyl, ethylthiomethyl, and propylthiomethyl.
The term "$C_{1-6}$ alkoxy $C_{1-6}$ alkyl group" refers to $C_{1-6}$ alkyloxy $C_{1-6}$ alkyl groups such as methoxymethyl and 1-ethoxyethyl.
The ar($C_{1-6}$)alkyloxy $C_{1-6}$ alkyl group refers to ar($C_{1-6}$)alkyloxy $C_{1-6}$ alkyl groups such as benzyloxymethyl and phenethyloxymethyl.
The term "$C_{1-6}$ alkoxy group" refers to linear or branched $C_{1-6}$ alkyloxy groups such as methoxy, ethoxy, propoxy, isopropoxy, butoxy, isobutoxy, tert-butoxy, pentyloxy, and hexyloxy.
The term "$C_{2-6}$ alkenyloxy group" refers to $C_{2-6}$ alkenyloxy groups such as vinyloxy, propenyloxy, butenyloxy, pentenyloxy, and hexenyloxy.
The term "$C_{1-6}$ alkylthio group" refers to $C_{1-6}$ alkylthio groups such as methylthio, ethylthio, propylthio, isopropylthio, butylthio, isobutylthio, tert-butylthio, pentylthio, and hexylthio.
The term "aryl group" refers to a phenyl, naphthyl, indanyl, or indenyl group.
The term "aryloxy group" refers to a phenyloxy, naphthyloxy, indanyloxy, or indenyloxy group.
The term "ar($C_{1-6}$)alkyl group" refers to ar($C_{1-6}$)alkyl groups such as benzyl, diphenylmethyl, trityl, and phenethyl.
The term "arylthio group" refers to a phenylthio, naphthylthio, indanylthio, or indenylthio group.

The term "acyl group" refers to $C_{2-6}$ alkanoyl groups such as formyl, acetyl, isovaleryl, propionyl, and pivaloyl, ar(C1-6)alkylcarbonyl groups such as benzylcarbonyl, or aroyl groups such as benzoyl and naphthoyl.

The term "$C_{1-6}$ alkyloxycarbonyl group" refers to linear or branched $C_{1-6}$ alkyloxycarbonyl groups such as methoxycarbonyl, ethoxycarbonyl, 1,1-dimethylpropoxycarbonyl, isopropoxycarbonyl, 2-ethylhexyloxycarbonyl, tert-butoxycarbonyl, and tert-pentyloxycarbonyl.

The term "ar($C_{1-6}$)alkyloxycarbonyl group" refers to ar($C_{1-6}$)alkyloxycarbonyl groups such as benzyloxycarbonyl and phenethyloxycarbonyl.

The term "aryloxycarbonyl group" refers to groups such as phenyloxycarbonyl.

The term "heterocyclic oxycarbonyl group" refers to groups such as 2-furfuryloxycarbonyl and 8-quinolyloxycarbonyl.

The term "$C_{1-6}$ alkylsulfonyl group" refers to $C_{1-6}$ alkylsulfonyl groups such as methylsulfonyl, ethylsulfonyl, and propylsulfonyl.

The term "arylsulfonyl group" refers to, for example, a phenylsulfonyl, p-toluenesulfonyl, or naphthylsulfonyl group.

The term "$C_{1-6}$ alkylamino group" refers to mono- or di-$C_{1-6}$ alkylamino groups such as methylamino, ethylamino, propylamino, isopropylamino, butylamino, dimethylamino, diethylamino, diisopropylamino, and dibutylamino.

The term "heterocyclic group" refers to a heterocyclic group such as a 5- or 6-membered ring, condensed ring, or bridged ring group containing at least one hetero atom selected from the group consisting of nitrogen, oxygen, and sulfur atoms. Examples of such heterocyclic group include pyrrolidinyl, piperidinyl, piperazinyl, homopiperazinyl, homopiperidinyl, morpholyl, thiomorpholyl, tetrahydroquinolinyl, tetrahydroisoquinolyl, quinuclidinyl, imidazolinyl, pyrrolyl, imidazolyl, pyrazolyl, pyridyl, pyrimidyl, quinolyl, quinolizinyl, thiazolyl, tetrazolyl, thiadiazolyl, pyrrolinyl, pyrazolinyl, pyrazolidinyl, purinyl, furyl, thienyl, benzothienyl, pyranyl, isobenzofuranyl, oxazolyl, isoxazolyl, benzofuranyl, indolyl, benzimidazolyl, benzoxazolyl, benzoisoxazolyl, benzothiazolyl, quinoxalyl, dihydro quinoxalyl, 2,3-dihydrobenzothienyl, 2,3-dihydrobenzopyrrolyl, 2,3-4H-1-thianaphtyl, 2,3-dihydrobenzofuranyl, benzo[b]dioxanyl, imidazo[2,3-a]pyridyl, benzo[b]piperazinyl, chromenyl, isothiazolyl, isoxazolyl, oxadiazolyl, pyridazinyl, isoindolyl, isoquinolyl, 1,3-benzodioxonyl, and 1,4-benzodioxanyl.

The term "oxygen-containing heterocyclic group" refers to groups such as 2-tetrahydropyranyl and 2-tetrahydrofuranyl.

The term "sulfur-containing heterocyclic group" refers to groups such as tetrahydrothiopyranyl.

The term "substituted silyl group" refers to groups such as trimethylsilyl, triethylsilyl, and tributylsilyl.

The term "$C_{1-6}$ alkylsilyl $C_{1-6}$ alkyl group" refers to groups such as 2-(trimethylsilyl)ethyl.

Examples of the amino-protecting group include all groups which can be used as usual protective groups for amino groups, for example, groups described in the W. Greene et al., Protective Groups in Organic Synthesis, the 4th edition, pp. 696 to 868, 2007, John Wiley & Sons, INC. Specific examples thereof include an acyl group, a $C_{1-6}$ alkyloxycarbonyl group, an ar($C_{1-6}$)alkyloxycarbonyl group, an aryloxycarbonyl group, an ar($C_{1-6}$)alkyl group, a $C_{1-6}$ alkoxy $C_{1-6}$ alkyl group, an ar($C_{1-6}$)alkyloxy $C_{1-6}$ alkyl group, an arylthio group, a $C_{1-6}$ alkylsulfonyl group, an arylsulfonyl group, and a substituted silyl group.

Examples of the hydroxyl-protecting group include all groups which can be used as usual protective groups for hydroxyl groups, for example, groups described in W. Greene et al., Protective Groups in Organic Synthesis, the 4th edition, pp. 16 to 299, 2007, John Wiley & Sons, INC. Specific examples thereof include an acyl group, a $C_{1-6}$ alkyloxycarbonyl group, an ar($C_{1-6}$) alkyloxycarbonyl group, a heterocyclic oxycarbonyl group, a $C_{1-6}$ alkyl group, a $C_{2-6}$ alkenyl group, an ar($C_{1-6}$)alkyl group, an oxygen-containing heterocyclic group, a sulfur-containing heterocyclic group, a $C_{1-6}$ alkoxy $C_{1-6}$ alkyl group, an ar($C_{1-6}$) alkyloxy $C_{1-6}$ alkyl group, a $C_{1-6}$ alkylsulfonyl group, an arylsulfonyl group, and a substituted silyl group.

Examples of the carboxyl-protecting group includes all groups that can be used as usual protective groups for carboxyl groups, for example, groups described in W. Greene et al., Protective Groups in Organic Synthesis, the 4th edition, pp. 533 to 643, 2007, John Wiley & Sons, INC. Specific examples thereof include a $C_{1-6}$ alkyl group, a $C_{2-6}$ alkenyl group, an aryl group, an ar($C_{1-6}$)alkyl group, an acyl $C_{1-6}$ alkyl group, an arylthio $C_{1-6}$ alkyl group, an arylsulfonyl $C_{1-6}$ alkyl group, an oxygen-containing heterocyclic group, a $C_{1-6}$ alkylsilyl $C_{1-6}$ alkyl group, an acyloxy $C_{1-6}$ alkyl group, a nitrogen-containing heterocyclic $C_{1-6}$ alkyl group, a $C_{3-8}$ cycloalkyl group, a $C_{1-6}$ alkoxy $C_{1-6}$ alkyl group, an ar($C_{1-6}$)alkyloxy $C_{1-6}$ alkyl group, a $C_{1-6}$ alkylthio $C_{1-6}$ alkyl group, and a substituted silyl group.

Examples of a substituent for $C_{1-6}$ alkyl group, an aryl group, an ar($C_{1-6}$)alkyl group, a $C_{1-6}$ alkoxy group, an aryloxy group, a $C_{1-6}$ alkylthio group, an arylthio group, a $C_{2-6}$ alkenyl group, a $C_{2-6}$ alkenyloxy group, a $C_{1-6}$ alkylamino group, a $C_{1-6}$ alkylsulfonyl group, an arylsulfonyl group, a carbamoyl group, and a heterocyclic group for $R^1$ and $R^2$ and a $C_{1-6}$ alkylamino group for $R^3$ include groups selected from among a halogen atom, a $C_{1-6}$ alkyl group, a $C_{3-8}$ cycloalkyl group, an aryl group, a $C_{1-6}$ alkoxy group, an aryloxy group, a $C_{1-6}$ alkylthio group, an arylthio group, a $C_{2-6}$ alkenyl group, a $C_{1-6}$ alkylsulfonyl group, an arylsulfonyl group, a $C_{1-6}$ alkylamino group, an optionally protected amino group, an optionally protected hydroxyl group, an optionally protected carboxyl group, an acyl group, and a heterocyclic group.

Examples of salts of the compound represented by the formula [1] include salts of basic groups such as generally known amino groups or acidic groups such as hydroxyl and carboxyl groups.

Salts of basic groups include: salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylene sulfonic acid, and naphthalene sulfonic acid.

Examples of salts of acidic groups include salts with alkaline metals such as sodium and potassium; salts with alkaline earth metals such as calcium and magnesium; ammonium salts; and salts with nitrogen-containing organic acids such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine, 1-Efenamin, and N,N'-dibenzylethylenediamine.

Among the salts described above, preferable salts include pharmacologically acceptable salts and more preferable salts include maleic acid.

In a case in which there exist isomers (e.g., optical isomers, geometric isomers, and tautomers) of an alkyl ether derivative represented by the formula [1] or a salt thereof, the present invention encompasses all these isomers and also encompasses hydrates, solvates, and any crystal forms thereof.

As an alkyl ether derivative represented by the formula [1] or a salt thereof used in the present invention, the following compounds are preferable examples.

A compound in which $R^1$ is a hydrogen atom, a halogen atom, or a $C_{1-6}$ alkoxy group is preferable, and a compound in which $R^1$ is a hydrogen atom is more preferable.

A compound in which $R^2$ is a hydrogen atom, a halogen atom, or a $C_{1-6}$ alkoxy group is preferable, and a compound in which $R^2$ is a hydrogen atom is more preferable.

A compound in which $R^3$ is an optionally protected hydroxyl group is preferable, and a compound in which $R^3$ is a hydroxyl group is more preferable.

A compound in which m is 2 and n is 2 or 3 is preferable, and a compound in which m is 2 and n is 3 is more preferable.

It is particularly preferable that an alkyl ether derivative represented by the formula [1] is 1-(3-(2-(1-benzothiophene-5-yl)ethoxy)propyl)azetidine-3-ol.

The present invention can be expected to be used in research to elucidate the roles of sigma receptors in various physiological and pathological pathways.

The alkyl ether derivative of the formula [1] or a salt thereof of the present invention can be used as a laboratory reagent or a reference substance used in experiments related to the sigma receptor activity. For example, the derivative or a salt thereof can be used for purification of sigma receptor fractions, screening of a new sigma receptor-binding, activating or inhibiting agent, and imaging of a sigma receptor.

When the alkyl ether derivative of the formula [1] or a salt thereof of the present invention is used in experiments, it is possible to dissolve the derivative or a salt thereof in a solvent (e.g., dimethyl sulfoxide) before use. It is also possible to use the derivative or a salt thereof with auxiliary agents (e.g., a stabilizer and a pH adjuster) or other pharmacological ingredients.

The present invention can be expected to be used for prevention and/or treatment of diseases in which sigma receptors are involved.

Drugs characterized by containing the alkyl ether derivative represented by the formula [1] or a salt thereof of the present invention can be used as agents for preventing and/or treating diseases where sigma receptors are involved.

A method of administering the alkyl ether derivative represented by the formula [1] or a salt thereof of the present invention to a subject can be used as a method of preventing and/or treating diseases where sigma receptors are involved.

The alkyl ether derivative represented by the formula [1] or a salt thereof of the present invention can be used for the production of agents for preventing and/or treating diseases where sigma receptors are involved.

Examples of diseases where sigma-1 receptors are involved include neurodegenerative diseases (e.g., Alzheimer's disease, Parkinson's disease, Huntington's chorea, amyotrophic lateral sclerosis (ALS), and Down's syndrome); cancer; ocular diseases (e.g., diabetic retinopathy and glaucoma); drug addiction; HIV encephalopathy; heart diseases (e.g., myocardial infarction, dilated cardiomyopathy, and heart failure); neuropathy (e.g., diabetic neuropathy, peripheral neuropathy such as neuropathy caused by cancer treatment, or Guillain-Barre syndrome); diabetic cardiomyopathy; peripheral nerve injury; spinal cord injury; spinal canal stenosis; multiple sclerosis; cerebral ischemic diseases; epilepsy; depression; anxiety; schizophrenia; tremor; restless legs syndrome; neuropathic pain (e.g., fibromyalgia, painful neuropathy, post-herpetic neuralgia, back pain, trigeminal neuralgia, carpal tunnel syndrome, phantom limb pain, spinal cord injury, or multiple sclerosis); chronic pain (e.g., cancer pain); numbness due to wound; autonomic defects (diabetic autonomic neuropathy, asymptomatic hypoglycemia, gastroparesis, neuropathic diarrhea and constipation, erectile dysfunction, orthostatic hypotension, arrhythmia, painless myocardial infarction, sweating abnormalities, neurogenic bladder, sudden deafness, chronic arterial obstruction, and hot flush); bladder dysfunction (e.g., bladder reflex disorder); hearing disorder; acoustic trauma-induced hearing loss; diabetic foot lesion; and Hirschsprung's disease.

Examples of diseases where sigma-2 receptors are involved include schizophrenia, Alzheimer's disease, and cancer.

The alkyl ether derivative represented by the formula [1] or a salt thereof used in the present invention can be produced by publicly known methods or any appropriate combination thereof or by the method described in Patent Literature 1.

The alkyl ether derivative represented by the formula [1] or a salt thereof used in the present invention can be obtained as pharmaceutical preparations such as oral preparations (e.g., tablets, capsules, powders, granules, fine granules, pills, suspensions, emulsions, liquids, and syrups), injections, and eye drops by blending various pharmaceutical additives such as an excipient, a binding agent, a disintegrating agent, a disintegration inhibitor, a consolidation/adhesion-preventing agent, a lubricant, an absorption/adsorption carrier, a solvent, a bulking agent, an isotonic agent, a solubilizer, an emulsifier, a suspending agent, a thickener, a coating agent, an absorption enhancer, a gelling/procoagulant agent, a light stabilizer, a preservative, a desiccant, an emulsification/suspension/dispersion stabilizer, a color protecting agent, a deoxidant/antioxidant, a flavoring agent, a coloring agent, a foaming agent, an antifoaming agent, a soothing agent, an antistatic agent, a buffer, and/or a pH adjuster.

The above various drugs are prepared by conventional methods.

Oral solid preparations such as tablets, powders, and granules may be formulated according to conventional methods using the following pharmaceutical additives for solid preparations for example: excipients such as lactose, sucrose, sodium chloride, glucose, starch, calcium carbonate, kaolin, crystalline cellulose, anhydrous dibasic calcium phosphate, partially pregelatinized starch, corn starch, and alginic acid; binding agents such as a simple syrup, a glucose solution, a starch solution, a gelatin solution, polyvinyl alcohol, polyvinyl ether, polyvinylpyrrolidone, carboxymethylcellulose, shellac, methylcellulose, ethylcellulose, sodium alginate, gum arabic, hydroxypropylmethylcellulose, hydroxypropylcellulose, water, and ethanol; disintegrating agents such as dry starch, alginic acid, agar powder, starch, crosslinked polyvinylpyrrolidone, crosslinked sodium carboxymethyl cellulose, carboxymethylcellulose calcium, and sodium starch glycolate; disintegration inhibitors such as stearyl alcohol, stearic acid, cacao butter, and hydrogenated oil; consolidation/adhesion-preventing agents such as aluminum silicate, calcium hydrogen phosphate, magnesium oxide, talc, and anhydrous silicic acid; lubricants such as carnauba wax, light anhydrous silicic acid, aluminum silicate, magnesium silicate, hardened oil, a hydrogenated vegetable oil derivative, sesame oil, bleached beeswax, titanium oxide, dried aluminum hydroxide gel, stearic acid, calcium stearate, magnesium stearate, talc, calcium hydrogen phosphate, sodium lauryl sulfate, and polyethylene glycol; absorption enhancers such as a quarterly ammonium salt, sodium lauryl sulfate, urea, and an enzyme; absorption/adsorption carriers such as starch, lactose, kaolin, bentonite, silicic acid anhydride, hydrated silicon dioxide, magnesium aluminometasilicate, and colloidal silicic acid.

Further, if necessary, tablets may be prepared as tablets with conventional coatings such as sugar-coated tablets, gelatin-coated tablets, stomach-soluble coated tablets, enteric-soluble coated tablets, and water-soluble film coated tablets.

Capsules are prepared by mixing the compound or a salt thereof with various pharmaceutical products exemplified above and filling capsules such as hard gelatin capsules and soft capsules with the mixture.

Furthermore, it is also possible to obtain various preparations such as water-based or oil-based suspensions, solutions, syrups, and elixirs with the use of the various liquid preparation additives described above, such as solvents, bulking agents, isotonic agents, solubilizers, emulsifiers, suspending agents, and thickeners according to a conventional method.

Injections can be prepared according to conventional methods using the following pharmaceutical additives for liquid preparations: diluents such as water, ethyl alcohol, macrogol, propylene glycol, citric acid, acetic acid, phosphoric acid, lactic acid, sodium lactate, sulfuric acid, and sodium hydroxide; pH adjusters and buffers such as sodium citrate, sodium acetate, and sodium phosphate; stabilizers such as sodium pyrosulfite, ethylenediamine tetraacetate, thioglycolic acid, and thiolactic acid; isotonic agents such as sodium chloride, glucose, and mannitol or glycerin; solubilizers such as sodium carboxymethyl cellulose, propylene glycol, sodium benzoate, benzyl benzoate, urethane, ethanolamine, and glycerin; soothing agents such as calcium gluconate, chlorobutanol, glucose, and benzyl alcohol; and local anesthetics.

Eye drops can be prepared according to conventional methods by optionally blending the following agents: preservatives such as chlorobutanol, sodium dehydroacetate, benzalkonium chloride, cetylpyridinium chloride, phenethyl alcohol, methyl parahydroxybenzoate, and benzethonium chloride; buffers such as borax, boric acid, and potassium dihydrogen phosphate; thickeners such as methylcellulose, hydroxyethyl cellulose, carboxymethyl cellulose, hydroxypropylmethyl cellulose, polyvinyl alcohol, sodium carboxymethyl cellulose, and chondroitin sulfate: solubilizers such as polysorbate 80 and polyoxyethylene hydrogenated castor oil 60; stabilizers such as sodium edetate and sodium bisulfite; and isotonic agents such as sodium chloride, potassium chloride, and glycerin.

Methods of administering the above preparations are not particularly limited. However, they may be appropriately determined depending on preparation forms, patient's age, sex, and other conditions, and severity of patient's symptoms.

The dosages of the active ingredients of the preparations may be appropriately determined depending on dose regimens, patient's age and sex, disease morphology, and other conditions. However, the preparations may be administered once or in divided times a day at a dose of 0.1 to 1000 mg for an adult. Preferably, the amount of 40 to 500 mg may be administered in a single dose or several divided doses.

EXAMPLES

The present invention will be described in the following test examples below. However, these examples are not intended to limit the scope of the present invention.

As a test substance, 1-(3-(2-(1-benzothiophene-5-yl)ethoxy)propyl)azetidine-3-ol maleate (hereinafter referred to as "compound A") was used.

Test Example 1 (Receptor Binding Assay)

The compound A was tested for ability to bind to 21 types of receptors. Each receptor was tested by a method described below in accordance with the corresponding one of the following: $\alpha_1$ (non-selective): Greengrass and Bremner (1979); $\alpha_2$ (non-selective): Uhlen and Wikberg (1991); $\beta_1$ (h): Smith and Teitler (1999); $\beta_2$: Abrahamsson et al. (1988); $AT_1$ (h): Bergsma et al. (1992); $AT_2$ (h): Tsuzuki et al. (1994); BZD (central): Speth et al. (1979); D1: Trampus et al. (1991); D2: Terai et al. (1989); $GABA_A$: Snodgrass (1978); $GABA_B$: Bowery et al. (1983), NMDA: Sills et al. (1991); $H_1$ (h): Smit et al. (1996); $H_2$: Ruat et al. (1990); $M_1$: Watson et al. (1982); $M_2$ (h): Dorje et al. (1991); N (neuronal) (α-BGTX-insensitive): Pabreza et al. (1991); 5-HT (non-selective): Peroutka and Snyder (1979); σ (non-selective): Shirayama et al. (1993); TH: Inoue et al. (1983); and TRH: Sharif and Burt (1983).

Table 1 lists the receptors and reference compounds used in the assay.

TABLE 1

| Receptor | Origin | Reference compound |
|---|---|---|
| $\alpha_1$ (non-selective) | rat cerebral cortex | prazosin |
| $\alpha_2$ (non-selective) | rat cerebral cortex | yohimbine |
| $\beta_1$ (h) | human recombinant (Sf9 cells) | atenolol |
| $\beta_2$ | guinea-pig lung | ICI118551 |
| $AT_1$ (h) | human recombinant (CHO cells) | saralasin |
| $AT_2$ (h) | human recombinant (Hela cells) | saraiasin |
| BZD (central) | rat cerebral cortex | diazepam |
| D1 | rat striatum | SCH23390 |
| D2 | rat striatum | (+)-butaclamol |
| $GABA_A$ | rat cerebral cortex | muscimol |
| $GABA_B$ | rat cerebral cortex | baclofen |
| NMDA | rat cerebral cortex | CGS19755 |
| $H_1$ (h) | human recombinant (HEK-293 cells) | pyrilamine |
| $H_2$ | guinea-pig striatum | cimetidine |
| $M_1$ | rat cerebral cortex | pirenzepine |
| $M_2$ (h) | human recombinant (CHO cells) | methoctramine |
| N (neuronal) (α-BGTX-insensitive) | rat cerebral cortex | nicotine |
| 5-HT (non-selective) | rat cerebral cortex | serotonin |
| σ non-selective | rat cerebral cortex | haloperidol |
| TH | rat liver | $T_3$ |
| TRH | rat cerebral cortex | TRH |

The test was conducted using the compound A at 10 μM.

Table 2 lists the reference compounds and radioligands for the respective receptors (each figure in parentheses indicates the final concentration) and incubation conditions.

TABLE 2

| Receptor | Radioligand | Reference compound | Incubation condition |
|---|---|---|---|
| $\alpha_1$ (non-selective) | [$^3$H] prazosin (0.25 nM) | prazosin (0.5 μM) | 60 min./22° C |
| $\alpha_2$ (non-selective) | [$^3$H] RX 821002 (0.5 nM) | (−)-epinephrine (100 μM) | 30 min./22° C. |
| $\beta_1$ (h) | [$^3$H] (−)CGP 12177 (0.15 nM) | alprenolol (50 μM) | 60 min./22° C. |
| $\beta_2$ | [$^3$H] (−)CGP 12177 (+10 nM CGP 20712A) (0.4 nM) | alprenolol (50 μM) | 40 min./22° C. |
| $AT_1$ (h) | [$^{125}$I] [Sar$^1$, Ile$^5$]-AT II (0.05 nM) | angiotensin I (10 μM) | 60 min./37° C. |
| $AT_2$ (h) | [$^3$H] GCP 42112A (0.05 nM) | angiotensin II (1 μM) | 180 min./37° C. |
| BZD (central) | [$^3$H] flunitrazepam (0.4 nM) | diazepam (3 μM) | 60 min./4° C. |
| D1 | [$^3$H] SCH 23390 (0.3 nM) | SCH 23390 (10 μM) | 45 min./22° C. |
| D2 | [$^3$H] YM-09151-2 (0.1 nM) | (+)-butaclamol (10 μM) | 60 min./22° C. |
| $GABA_A$ | [$^3$H] muscimol (5 nM) | muscimol (10 μM) | 10 min./4° C. |
| $GABA_B$ | [$^3$H] GABA (+40 μM isoguvacine) (10 nM) | baclofen (100 μM) | 10 min./22° C. |
| NMDA | [$^3$H] CGP 39653 (5 nM) | L-glutamate (100 μM) | 60 min./4° C. |
| $H_1$ (h) | [$^3$H] pyrilamine (3 nM) | pyrilamine (1 μM) | 60 min./22° C. |
| $H_2$ | [$^3$H] APT (0.1 nM) | tiotidine (100 μM) | 150 min/22° C. |
| $M_1$ | [$^3$H] pirenzepine (1 nM) | atropine (1 μM) | 60 min./22° C. |
| $M_2$ (h) | [$^3$H] AF-DX 384 (2 nM) | atropine (1 μM) | 60 min./22° C. |
| N (neuronal) (α-BGTX-insensitive) | [$^3$H] cytisine (1.5 nM) | nicotine (10 μM) | 75 min./4° C. |
| 5-HT (non-selective) | [$^3$H] serotonin (2 nM) | serotonin (10 μM) | 15 min./37° C. |
| σ (non-selective) | [$^3$H] DTG (8 nM) | haloperidol (10 μM) | 120 min./22° C. |
| TH | [$^{125}$I] $T_3$ (0.1 nM) | $T_3$ (1 μM) | 18 h/4° C. |
| TRH | [$^3$H] Me-TRH (2 nM) | TRH (30 μM) | 6 h/4° C. |

The inhibition rate of the compound A for each radioligand was calculated by the following equation.

$$100-([\text{measured specific binding}]/[\text{control specific binding}] \times 100) \quad \text{Equation:}$$

In the equation, the measured specific binding indicates the amount of binding radioactivity of each radioligand under the presence of the compound A and the corresponding reference compound, and the control specific binding indicates the amount of binding radioactivity of each radioligand under the presence of the corresponding reference compound.

Table 3 shows the results.

The compound A was found to selectively have a high affinity for sigma receptors.

TABLE 3

| Receptor | Inhibition rate of compound A for radioligand (%) |
|---|---|
| $\alpha_1$ (non-selective) | 36 |
| $\alpha_2$ (non-selective) | 40 |
| $\beta_1$ (h) | 10 |
| $\beta_2$ | 5 |
| $AT_1$ (h) | −2 |
| $AT_2$ (h) | −13 |

TABLE 3-continued

| Receptor | Inhibition rate of compound A for radioligand (%) |
|---|---|
| BZD (central) | 25 |
| D1 | 1 |
| D2 | 21 |
| $GABA_A$ | −8 |
| $GABA_B$ | 4 |
| NMDA | 16 |
| $H_1$ (h) | −15 |
| $H_2$ | 72 |
| $M_1$ | 43 |
| $M_2$ (h) | 19 |
| N (neuronal) (α-BGTX-insensitive) | 12 |
| 5-HT (non-selective) | 2 |
| σ (non-selective) | 99 |
| TH | −5 |
| TRH | 1 |

Test Example 2 (Identification of Sigma-1 Receptor Inhibition Constant)

The sigma-1 receptor inhibition constant of the compound A (Ki value) was identified. The test was conducted by a method described below in accordance with Ganapathy, M. E. (1999).

In the sigma-1 receptors expressed in Jurkat cells, the inhibition rate of the compound A was measured at different concentrations (0.1, 0.3, 1, 3, 10, 30, 100, 300, and 1000 nM) for 15 nM [$^3$H] (+)-pentazocine. The reaction was conducted at 37° C. for 120 minutes. The inhibition rate was calculated in the same manner as described in Test Example 1. The Ki value was identified in accordance with the Cheng-Prusoff equation by calculating IC$_{50}$ based on nonlinear regression analysis.

As a result, the Ki value of the compound A was 16 nM.

Test Example 3 (Identification of Sigma-2 Receptor Inhibition Constant)

The sigma-2 receptor inhibition constant of the compound A (Ki value) was identified. The test was conducted by a method described below in accordance with Ganapathy, M. E. (1999).

In the sigma-2 receptors expressed in Jurkat cells, the inhibition rate of the compound A was measured at different concentrations (0.1, 0.3, 1, 3, 10, 30, 100, 300, and 1000 nM) for 25 nM [$^3$H] DTG under the presence of 1 μM (+)-pentazocine. The reaction was conducted at room temperature for 60 minutes. The inhibition rate was calculated in the same manner as described in Test Example 1. The Ki value was identified in accordance with the Cheng-Prusoff equation by calculating IC$_{50}$ based on nonlinear regression analysis.

As a result, the Ki value of the compound A was 160 nM.

INDUSTRIAL APPLICABILITY

The alkyl ether derivative represented by the formula [1] or a salt thereof of the present invention exhibited a high affinity for sigma receptors and thus is useful as a sigma receptor-binding agent.

A method of using the alkyl ether derivative represented by the formula [1] or a salt thereof of the present invention is useful as a method of activating or inhibiting a sigma receptor.

The invention claimed is:

1. A method for inhibition of a sigma receptor, which comprises administering an alkyl ether derivative represented by the formula [1] or a salt thereof to a subject in need of inhibition of a sigma receptor:

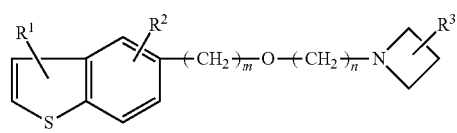

[1]

wherein $R^1$ and $R^2$, which are the same or different, each represent at least one member selected from the group consisting of a hydrogen atom, a halogen atom, an optionally substituted $C_{1-6}$ alkyl group, an optionally substituted aryl group, an optionally substituted ar($C_{1-6}$)alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group, and an oxo group; $R^3$ represents an optionally substituted $C_{1-6}$ alkylamino group, an optionally protected amino group, or an optionally protected hydroxyl group; m and n, which are the same or different, each represent an integer of 1 to 6.

2. A method for inhibition of a sigma receptor, which comprises administering an alkyl ether derivative represented by the formula [1] or a salt thereof to a subject in need of inhibition of a sigma-1 receptor:

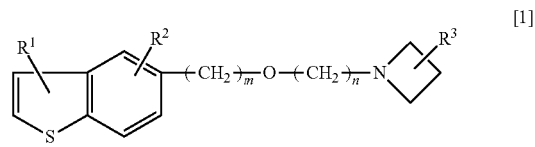

[1]

wherein $R^1$ and $R^2$, which are the same or different, each represent at least one member selected from the group consisting of a hydrogen atom, a halogen atom, an optionally substituted $C_{1-6}$ alkyl group, an optionally substituted aryl group, an optionally substituted ar($C_{1-6}$)alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group, and an oxo group; $R^3$ represents an optionally substituted $C_{1-6}$ alkylamino group, an optionally protected amino group, or an optionally protected hydroxyl group; m and n, which are the same or different, each represent an integer of 1 to 6.

3. The method according to claim 2, wherein $R^1$ and $R^2$, which are the same or different, each represent a hydrogen atom, a halogen atom, or a $C_{1-6}$ alkoxy group.

4. The method according to claim 2, wherein m is 2 and n is 2 or 3.

5. The method according to claim 3, wherein m is 2 and n is 2 or 3.

6. The method according to claim 2, wherein $R^3$ is an optionally protected hydroxyl group.

7. The method according to claim 3, wherein $R^3$ is an optionally protected hydroxyl group.

8. The method according to claim 4, wherein $R^3$ is an optionally protected hydroxyl group.

9. The method according to claim 5, wherein $R^3$ is an optionally protected hydroxyl group.

10. The method according to claim 2, wherein the alkyl ether derivative is 1-(3-(2-(1-benzothiophene-5-yl)ethoxy)propyl)azetidine-3-ol.

11. A method for inhibition of a sigma receptor, which comprises administering 1 (3 (2 (1 benzothiophene-5-yl)ethoxy)propyl)azetidine-3-ol or a salt thereof to a subject in need of inhibition of a sigma-2 receptor.

12. A method for investigating the physiological function and/or activity of sigma receptors, which comprises
(i) labeling an alkyl ether derivative represented by the formula [1] or a salt thereof with a label compound;
(ii) administering the labeled alkyl ether derivative or a salt thereof to cells and/or living body; and
(iii) imaging a distribution of sigma receptor in cells and/or living body by ray and/or radiation which is released from the label compound:

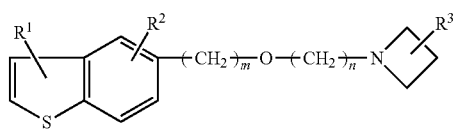

[1]

wherein $R^1$ and $R^2$, which are the same or different, each represent at least one member selected from the group consisting of a hydrogen atom, a halogen atom, an optionally substituted $C_{1-6}$ alkyl group, an optionally substituted aryl group, an optionally substituted ar($C_{1-6}$)alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group, and an oxo group; $R^3$ represents an optionally substituted $C_{1-6}$ alkylamino group, an optionally protected amino group, or an optionally protected hydroxyl group; m and n, which are the same or different, each represent an integer of 1 to 6.

13. A method for inhibition of a sigma receptor, which comprises
(i) identifying a subject in need of inhibition of a sigma receptor by analyzing an expression of sigma receptor gene in a subject and/or measuring an activity of sigma receptor in a subject; and
(ii) administering an alkyl ether derivative represented by the formula [1] or a salt thereof to the subject in need of inhibition of a sigma receptor:

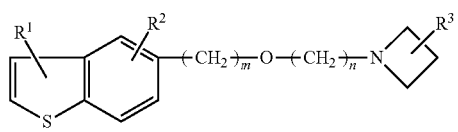

[1]

wherein $R^1$ and $R^2$, which are the same or different, each represent at least one member selected from the group consisting of a hydrogen atom, a halogen atom, an optionally substituted $C_{1-6}$ alkyl group, an optionally substituted aryl group, an optionally substituted ar($C_{1-6}$)alkyl group, an optionally substituted $C_{1-6}$ alkoxy group, an optionally substituted aryloxy group, an optionally substituted $C_{1-6}$ alkylthio group, an optionally substituted arylthio group, an optionally substituted $C_{2-6}$ alkenyl group, an optionally substituted $C_{2-6}$ alkenyloxy group, an optionally substituted $C_{1-6}$ alkylamino group, an optionally substituted $C_{1-6}$ alkylsulfonyl group, an optionally substituted arylsulfonyl group, an optionally substituted carbamoyl group, an optionally substituted heterocyclic group, an optionally protected amino group, an optionally protected hydroxyl group, an optionally protected carboxyl group, a nitro group, and an oxo group; $R^3$ represents an optionally substituted $C_{1-6}$ alkylamino group, an optionally protected amino group, or an optionally protected hydroxyl group; m and n, which are the same or different, each represent an integer of 1 to 6.

* * * * *